(12) United States Patent
Abbas

(10) Patent No.: US 10,349,661 B1
(45) Date of Patent: Jul. 16, 2019

(54) SYNTHETIC ANIMAL URINE ATTRACTANT

(71) Applicant: Greg A Abbas, Beaverton, MI (US)

(72) Inventor: Greg A Abbas, Beaverton, MI (US)

(73) Assignee: A-WAY HUNTING PRODUCTS, Inc., Beaverton, MI (US)

( * ) Notice: Subject to any disclaimer, the term of this patent is extended or adjusted under 35 U.S.C. 154(b) by 0 days.

(21) Appl. No.: 15/625,864

(22) Filed: Jun. 16, 2017

(51) Int. Cl.
| | | |
|---|---|---|
| *A01M 31/00* | (2006.01) | |
| *A01N 31/02* | (2006.01) | |
| *A01N 31/08* | (2006.01) | |
| *A01N 37/10* | (2006.01) | |
| *A01N 59/00* | (2006.01) | |
| *A01N 65/06* | (2009.01) | |
| *A01N 65/16* | (2009.01) | |

(52) U.S. Cl.
CPC ........... *A01N 65/16* (2013.01); *A01M 31/008* (2013.01); *A01N 31/02* (2013.01); *A01N 31/08* (2013.01); *A01N 37/10* (2013.01); *A01N 59/00* (2013.01); *A01N 65/06* (2013.01)

(58) Field of Classification Search
CPC ........ A01N 31/08; A01N 37/10; A01N 31/02; A01N 59/00; A01N 65/06; A01N 65/16; A01N 25/02; A01M 31/008
See application file for complete search history.

(56) References Cited

U.S. PATENT DOCUMENTS

| | | | |
|---|---|---|---|
| 6,231,849 B1 * | 5/2001 | Schiller | A01M 31/008 424/405 |
| 6,514,116 B2 | 2/2003 | Abbas | |
| 6,855,313 B1 | 2/2005 | Parrigan | |
| 7,073,732 B2 | 7/2006 | Abbas et al. | |
| 2008/0279811 A1 * | 11/2008 | Potgeter | A01N 25/18 424/84 |
| 2017/0099839 A1 * | 4/2017 | Healy | B05B 11/041 |

OTHER PUBLICATIONS

Jan M. Bakke and Erik Figenschou, "Volatile Compounds From the Red Deer (Cervus elaphus) Secretion from the Tail Gland", Journal of Chemical Ecology, vol. 9, No. 4, 1983, 513-520. (Year: 1983).*

* cited by examiner

*Primary Examiner* — John Pak
*Assistant Examiner* — Nathan W Schlientz
(74) *Attorney, Agent, or Firm* — Technology Law PLLC; Karen L. Kimble

(57) ABSTRACT

The present invention concerns synthetic urine as a game animal attractant, its method of use and the process to make it.

9 Claims, No Drawings

SYNTHETIC ANIMAL URINE ATTRACTANT

BACKGROUND OF THE INVENTION

Field of the Invention

This invention generally concerns the field of animal attractants for hunting and particularly the use of synthetic urine to attract deer, elk, hog, and other animal smells that can be male or female

Description of Related Art

U.S. Pat. No. 7,073,732 describes a method and apparatus for distributing a chemical composition for hunting animals. The chemical composition is distributed in the form of a foam string from an aerosol can.

U.S. Pat. No. 6,855,313 describes animal attractant made from a mixture of human urine and animal urine, especially deer.

Hunters are always trying to find their quarry, often deer, elk, hog or other land animals desired as game. Many hunters wander around hoping to encounter the desired animal, or they try to study the animals' habits to determine where they would likely be, or they put out bait to have the desired animal feed at the spot with the bait where they can monitor the times they appear. These techniques are only marginally useful and can take a lot of time to have happen.

An easier way to find the desired animal is to use a call apparatus (for example for deer a deer calling, rattling horns or grunt tube) or an attractant, usually urine based or having the desired scent, to have the animal come to the hunter. Some of the drawbacks to these methods are the size and effectiveness of the call apparatus to carry for the hunter for the desired game animal or the amount used and duration of the attractant required. Of course, expense is also an issue. There are several synthetic deer attractants on the market, but they all have drawbacks as most of them are water based and wash away easily with rain, dew or any moisture. Many such attractants are also ammonia based and does not smell like urine. The most common synthetic urine is the use of urea, diluted with water and then ammonia added to stabilize the mixture. This is not very true to the scent wanted.

Clearly, finding synthetic urine to use as an attractant makes the chemical reproducible in sufficient quantities and at low cost.

BRIEF SUMMARY OF THE INVENTION

The present invention provides a synthetic animal urine formulation where the scent lasts longer, is economical to make, and less is needed to be used as it is more potent than known scents. Thus the hunter does not need to carry has much attractant into the game site as needed by other attractants. Although each scent has its own components to obtain the desired attractant for the game animal, the procedure for its preparation and use is the same. Land animals as quarry can be deer, elk, hog and others of interest to a hunter. Each has its own attractant.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

The following terms as used in this application are to be defined as stated below and for these terms, the singular includes the plural.

Attractant means a scent used to attract a desired game animal to a hunter.

Hexylene glycol means 2-methyl-2,4-pentanediol.

Synthetic urine means an attractant that is made chemically without any naturally occurring urine present.

Discussion

The present invention relates to the preparation of synthetic animal urines as an attractant, its formulation, and method of use.

The present formulation comprises:

| Compound | % by weight (% wt.) |
| --- | --- |
| Hexylene glycol | 12-58 |
| Cresol mixture of isomers | 2-41 |
| Benzyl benzoate | 1-4 |
| Phenylacetic acid | 3-19 |
| cis-3-Hexenyl phenylacetate | 0-9 |
| p-Cresol | 0-41 |
| Isobutyl phenylacetate | 0-8 |
| Cedarwood essential oil | 0-6 |
| p-Cresyl caprylate | 0-4 |
| Oil of wintergreen | 0-1 |
| Ammonium hydroxide | 0-10 |
| Total | 100 | wherein: the total of all compounds is 10% by weight. Thus the compounds are selected within the stated ranges to equal 100% wt. The Hexylene glycol serves as the solvent. Because it is not a water based attractant, it can last for days and is not easily washed away by rain or moisture.

The formulation is prepared generally by mixing the compounds with a disc mixer equipped with a dispersion blade at low speed. A respirator and protective gear are required during mixing. The compounds are added in the order listed in the table below on low agitation. After all the compounds are added, the mixer is adjusted to medium speed and mixing continued for about 9-11 minutes. Optionally the mixture is then filtered to remove any solids such as by using a 100 micron nylon bag or optionally heated to dissolve any solids or compounds or both. The attractant mixture is then ready to be bottled, put into a spray bottle or an aerosol can for use.

The attractant is used as a liquid that is poured, as a spray in a spray bottle or as an aerosol can and applied outdoors for any desired game animal. For deer apply onto deer scrapes, deer trails, near deer feeders, or near the deer blind or other hangouts to bring the deer into view for a shot opportunity.

The invention will be further clarified by a consideration of the following examples, which are intended to be purely exemplary of the invention.

Example 1: Dominant Buck #1

This attractant has the odor of the buck's tarsal gland with a lesser urine smell mixed in. The attractant has the following formula:

| Compound | Grams (g) | % by weight (% wt.) |
| --- | --- | --- |
| Hexylene glycol | 55.2 | 55.2 |
| Cresol Mixture of isomers | 29.5 | 29.5 |
| Benzyl Benzoate | 2.9 | 2.9 |
| Phenylacetic acid | 4.8 | 4.8 |
| cis-3-Hexenyl phenylacetate | 7.6 | 7.6 |
| Total | 100 | 100 |

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The mixture is then filtered using a 100 micron nylon bag. The attractant mixture is then ready to be bottled, put into a spray bottle or an aerosol can for use.

This attractant is poured onto a scrape or other deer hangout to introduce an intruder buck scent into the area and make bucks in that area think that another buck has encroached into their territory; thus attracting them when they come looking for a fight.

Example 2: Urine 1

This attractant has the odor of urine with a slight gland smell to have a doe or younger buck urine smell.

| Compound | Grams (g) | % by weight (% wt.) |
| --- | --- | --- |
| p-Cresol* | 37.9 | 37.9 |
| Cresol mixture of isomers | 26.5 | 26.5 |
| Hexylene glycol | 14.5 | 14.5 |
| Phenylacetic acid | 17.3 | 17.3 |
| Isobutyl phenylacetate | 1.9 | 1.9 |
| Cedarwood essential oil | 1.9 | 1.9 |
| Total | 100 | 100 |

*from penta

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The attractant mixture is then ready to be bottled, put into a spray bottle or an aerosol can for use.

Example 3: Estrus Doe

This attractant has a very strong urine smell to use at the peak of the rut.

| Compound | Grams (g) | % by weight (% wt.) |
| --- | --- | --- |
| Hexylene glycol | 14.5 | 14.5 |
| p-Cresol | 39.0 | 39.0 |
| Cresol mixture of isomers | 22.4 | 22.4 |
| Phenylacetic acid | 17.3 | 17.3 |
| Cedarwood essential oil | 1.9 | 1.9 |
| Isobutyl phenylacetate | 1.9 | 1.9 |
| p-Cresyl caprylate | 3.0 | 3.0 |
| Total | 100 | 100 |

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The attractant mixture is then ready to be bottled, put into a spray bottle or an aerosol can for use.

Example 4: Urine 2

This attractant is a stronger version of Urine 1, in Example 2, to be used as rut approaches.

| Compound | Grams (g) | % by weight (% wt.) |
| --- | --- | --- |
| Hexylene glycol | 30.8 | 30.8 |
| Cresol mixture of isomers | 39.1 | 39.1 |
| Benzyl benzoate | 2.5 | 2.5 |
| Phenylacetic acid | 14.3 | 14.3 |
| Cedarwood essential oil | 5.0 | 5.0 |
| cis-3-Hexenyl phenylacetate | 1.6 | 1.6 |
| Isobutyl phenylacetate | 6.7 | 6.7 |
| Total | 100 | 100 |

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The attractant mixture is then ready to be bottled, put into a spray bottle or an aerosol can for use.

Example 5: Buck #2

This attractant is a stronger version of Buck #1, in Example 1, that gives the impression of yet another intruder buck into the area.

| Compound | Grams (g) | % by weight (% wt.) |
| --- | --- | --- |
| Hexylene glycol | 30.4 | 30.4 |
| Cresol mixture of isomers | 39.1 | 39.1 |
| Benzyl benzoate | 2.5 | 2.5 |
| Phenylacetic acid | 14.3 | 14.3 |
| Cedarwood essential oil | 5.0 | 5.0 |
| cis-3-Hexenyl phenylacetate | 1.6 | 1.6 |
| Oil of wintergreen | 0.4 | 0.4 |
| Isobutyl phenylacetate | 6.7 | 6.7 |
| Total | 100 | 100 |

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The attractant mixture is then ready to be bottled, put into a spray bottle or an aerosol can for use.

Example 6: Scrape Mix

This attractant has a strong smell of multiple urines and tarsal glands to give the impression of multiple deer frequenting the scrape area.

| Compound | Grams (g) | % by weight (% wt.) |
|---|---|---|
| Hexylene glycol | 40.4 | 40.4 |
| Cresol mixture of isomers | 29.5 | 29.5 |
| Benzyl benzoate | 2.5 | 2.5 |
| Phenylacetic acid | 14.3 | 14.3 |
| Cedarwood essential oil | 5.0 | 5.0 |
| cis-3-Hexenyl phenylacetate | 1.6 | 1.6 |
| Isobutyl phenylacetate | 6.7 | 6.7 |
| Total | 100 | 100 |

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The attractant mixture is then ready to be bottled, put into a spray bottle or an aerosol can for use.

Example 7: All Season

This attractant has the smell of urine with the added component of ammonia, as a by-product of urine, that allows the scent to work well all season long and especially in the pre- and post-rut time frames.

| Compound | Grams (g) | % by weight (% wt.) |
|---|---|---|
| Example 3 formulation | 90 | 90 |
| Ammonium hydroxide | 10 | 10 |
| Total | 100 | 100 |

The attractant of Example 3 above can have the attractant of Example 5 or 1 used instead to obtain a different All Season attractant.

The compounds are mixed with a disc mixer equipped with a dispersion blade at low speed. A respirator and protective gear are required during mixing. The compounds are added in the order listed in the above table on low agitation. After all the compounds are added, the mixer is adjusted to medium speed and mixing continued for about 9-11 minutes. The batch mixture is then covered with static free plastic to prevent solvent loss. The attractant mixture is then ready to be bottled, put into a spray bottle or an aerosol can for use.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A liquid formulation comprising:

| Compound | % by weight (% wt.) |
|---|---|
| Hexylene glycol | 12-58 |
| Cresol mixture of isomers | 2-41 |
| Benzyl benzoate | 0-4 |
| Phenylacetic acid | 3-19 |
| cis-3-Hexenyl phenylacetate | 0-9 |
| p-Cresol | 0-41 |
| Isobutyl phenylacetate | 0-8 |
| Cedarwood essential oil | 0-6 |
| p-Cresyl caprylate | 0-4 |
| Oil of wintergreen | 0-1 |
| Ammonium hydroxide | 0-10 |
| Total | 100 | wherein: the total of the compounds is selected to equal 100% by weight; and wherein the p-cresol is in addition to the cresol mixture of isomers.

2. The formulation of claim 1 wherein the hexylene glycol is present from 22 to 56% wt.; cresol mixture of isomers is present from 23 to 30% wt.; and the phenylacetic acid is present from 5 to 18% wt.

3. The formulation of claim 1 wherein the hexylene glycol is present at about 14.5% wt.; p-cresol is present at about 39.0% wt.: cresol mixture of isomers is present at about 22.4% wt.; phenylacetic acid is present at about 17.3% wt.; cedarwood essential oil is present at about 1.9% wt.; isobutyl phenylacetate is present at about 1.9% wt.; and p-cresyl caprylate is present at about 3.0% wt; and wherein the p-cresol is in addition to the cresol mixture of isomers.

4. The formulation of claim 1 wherein the hexylene glycol is present at about 40.4% wt.; cresol mixture of isomers is present at about 29.5% wt.; benzyl benzoate is present at about 2.5% wt.; phenylacetic acid is present at about 14.3% wt.; cedarwood essential oil is present at about 5.0% wt.; cis-3-hexenyl phenylacetate is present at about 1.6% wt.; and isobutyl phenylacetate is present at about 6.7% wt.

5. The formulation of claim 1 wherein the hexylene glycol is present at about 55.2% wt.; cresol mixture of isomers is present at about 29.5% wt.; benzyl benzoate is present at about 2.9% wt.: phenylacetic acid is present at about 4.8% wt.; and cis-3-hexenyl phenylacetate is present at about 7.6% wt.

6. A method of attracting Whitetail deer comprising applying the formulation of claim 1 outdoors, wherein the formulation is in the form of a liquid that is poured, as a spray in a spray bottle or as an active component in an aerosol can and applied outdoors for the Whitetail deer.

7. The method of claim 6 wherein the formulation is applied to attract Whitetail deer onto deer scrapes, deer trails, near deer feeders, or near the deer blind or other hangouts to bring the deer into view for a shot opportunity.

8. A process for preparing a formulation of claim 1 which comprises mixing the compounds with a disc mixer equipped with a dispersion blade at low speed while using a respirator and protective gear, then the mixer is adjusted to medium speed and mixing continued for about 9-11 minutes.

9. The process of claim 8 wherein the mixture is then filtered to remove any solids or optionally heated to dissolve any solids or compounds or both.

* * * * *